US009517169B2

(12) United States Patent
Nakakado

(10) Patent No.: US 9,517,169 B2
(45) Date of Patent: Dec. 13, 2016

(54) ULTRASONIC BONDING METHOD FOR ABSORBENT ARTICLE, ULTRASONIC BONDING DEVICE FOR ABSORBENT ARTICLE, AND ABSORBENT ARTICLE

(71) Applicant: Masaki Nakakado, Osaka (JP)

(72) Inventor: Masaki Nakakado, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 139 days.

(21) Appl. No.: 14/407,550

(22) PCT Filed: Jun. 13, 2013

(86) PCT No.: PCT/JP2013/066324
§ 371 (c)(1),
(2) Date: Dec. 12, 2014

(87) PCT Pub. No.: WO2014/007043
PCT Pub. Date: Jan. 9, 2014

(65) Prior Publication Data
US 2015/0148766 A1    May 28, 2015

(30) Foreign Application Priority Data

Jul. 4, 2012 (JP) .................. 2012-150140

(51) Int. Cl.
*A61F 13/15* (2006.01)
*A61F 13/535* (2006.01)
(Continued)

(52) U.S. Cl.
CPC ........ *A61F 13/535* (2013.01); *A61F 13/15203* (2013.01); *A61F 13/15634* (2013.01);
(Continued)

(58) Field of Classification Search
CPC ............ A61F 13/5323; A61F 13/15634; A61F 13/15642; A61F 13/15739; A61F 2013/530481; A61F 2013/53051; A61F 2013/530547; A61F 2013/530562; A61F 2013/15861; A61F 2013/15869; A61F 2013/15878; A61F 2013/15886; A61F 2013/15894; A61F 2013/15902; B29C 65/086; B29C 65/7894; B29C 66/21; B29C 66/232; B29C 66/234; B29C 66/433; B29C 66/436; B29C 66/7294; B29C 66/81433; B29C 66/83511; B29C 66/92451
See application file for complete search history.

(56) References Cited

U.S. PATENT DOCUMENTS 5,030,314 A * 7/1991 Lang ................. A61F 13/15634
156/390
7,694,644 B2 * 4/2010 Suzuki .............. A61F 13/15658
118/102
(Continued)

FOREIGN PATENT DOCUMENTS

CN      101426461 A     5/2009
JP      64-14301 A      1/1989
(Continued)

OTHER PUBLICATIONS

International Search report for corresponding International Application No. PCT/JP2013/066324 mailed Sep. 3, 2013.
(Continued)

*Primary Examiner* — Lynne Anderson
(74) *Attorney, Agent, or Firm* — Renner, Otto, Boisselle & Sklar, LLP

(57) ABSTRACT

An absorbent article having a plurality of granular particles placed between two liquid-permeable non-woven fabric sheets, the article including: a high-strength bonded portion formed in a loop-shaped pattern on the article such that the two non-woven fabric sheets are not separated even if the
(Continued)

granular particles swell to thereby apply a separating force to a bonded position between the two non-woven fabric sheets; and a low-strength bonded portion formed in an inner area surrounded by the high-strength bonded portion such that the two non-woven fabric sheets are separated from each other at a bonded position when the granular particles swell to thereby apply a separating force to the bonded position between the two non-woven fabric sheets.

4 Claims, 9 Drawing Sheets

(51) Int. Cl.
| | | |
|---|---|---|
| *B29C 65/08* | (2006.01) | |
| *B29C 65/78* | (2006.01) | |
| *B29C 65/00* | (2006.01) | |
| *A61F 13/532* | (2006.01) | |
| *A61F 13/539* | (2006.01) | |
| *B29L 31/48* | (2006.01) | |
| *A61F 13/53* | (2006.01) | |
| *A61F 13/534* | (2006.01) | |
| *B29C 65/76* | (2006.01) | |

(52) U.S. Cl.
CPC ...... *A61F 13/15707* (2013.01); *A61F 13/539* (2013.01); *A61F 13/5323* (2013.01); *B29C 65/086* (2013.01); *B29C 65/7847* (2013.01); *B29C 65/7894* (2013.01); *B29C 66/1122* (2013.01); *B29C 66/21* (2013.01); *B29C 66/232* (2013.01); *B29C 66/234* (2013.01); *B29C 66/433* (2013.01); *B29C 66/436* (2013.01); *B29C 66/7294* (2013.01); *B29C 66/7373* (2013.01); *B29C 66/81433* (2013.01); *B29C 66/83511* (2013.01); *B29C 66/92451* (2013.01); *A61F 2013/1539* (2013.01); *A61F 2013/15869* (2013.01); *A61F 2013/53051* (2013.01); *A61F 2013/53445* (2013.01); *A61F 2013/53991* (2013.01); *B29C 65/76* (2013.01); *B29C 66/73921* (2013.01); *B29C 66/83433* (2013.01); *B29L 2031/4878* (2013.01)

(56) References Cited

U.S. PATENT DOCUMENTS

| | | | |
|---|---|---|---|
| 7,744,713 B2* | 6/2010 | Blessing | A61F 13/15658 156/196 |
| 9,295,593 B2* | 3/2016 | Van Malderen | A61F 13/5323 |
| 2002/0095127 A1* | 7/2002 | Fish | A61F 13/5323 604/368 |
| 2007/0197987 A1 | 8/2007 | Tsang et al. | |
| 2012/0226253 A1 | 9/2012 | Urushihara | |
| 2013/0025795 A1* | 1/2013 | Ukegawa | A61F 13/15658 156/555 |
| 2013/0284361 A1 | 10/2013 | Tsujimoto et al. | |
| 2013/0284362 A1 | 10/2013 | Tsujimoto et al. | |

FOREIGN PATENT DOCUMENTS

| | | |
|---|---|---|
| JP | 2002-209930 A | 7/2002 |
| JP | 2007-130818 A | 5/2007 |
| JP | 2009-061230 A | 3/2009 |
| JP | 2011-136077 A | 7/2011 |
| WO | WO 95/11654 A1 | 5/1995 |
| WO | WO 2012/108330 A1 | 8/2012 |
| WO | WO 2012/108331 A1 | 8/2012 |
| WO | WO 2014/010365 A1 | 1/2014 |

OTHER PUBLICATIONS

Chinese Office Action dated Nov. 3, 2015 for corresponding Chinese Application No. 201380032205.1.

* cited by examiner

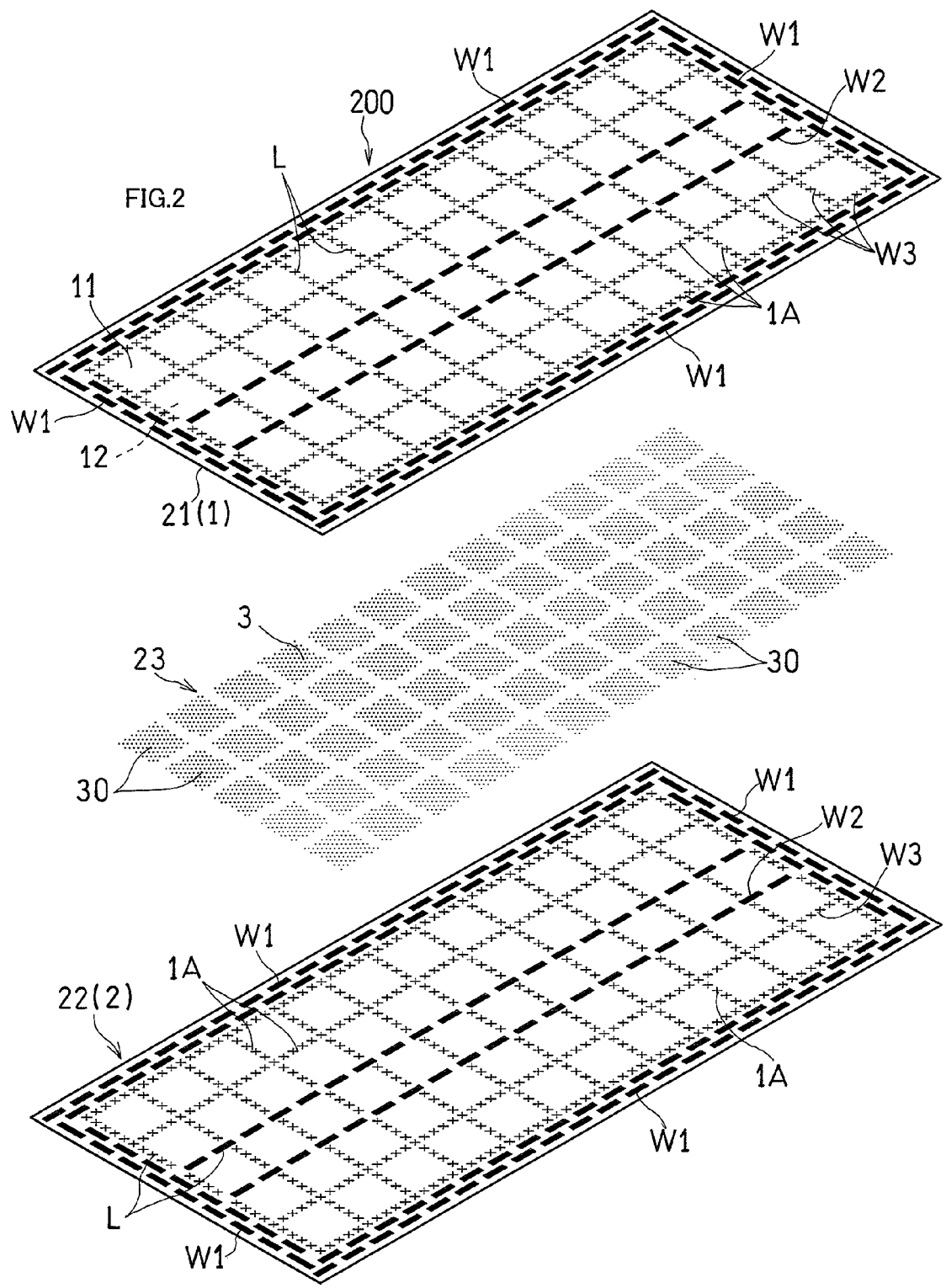

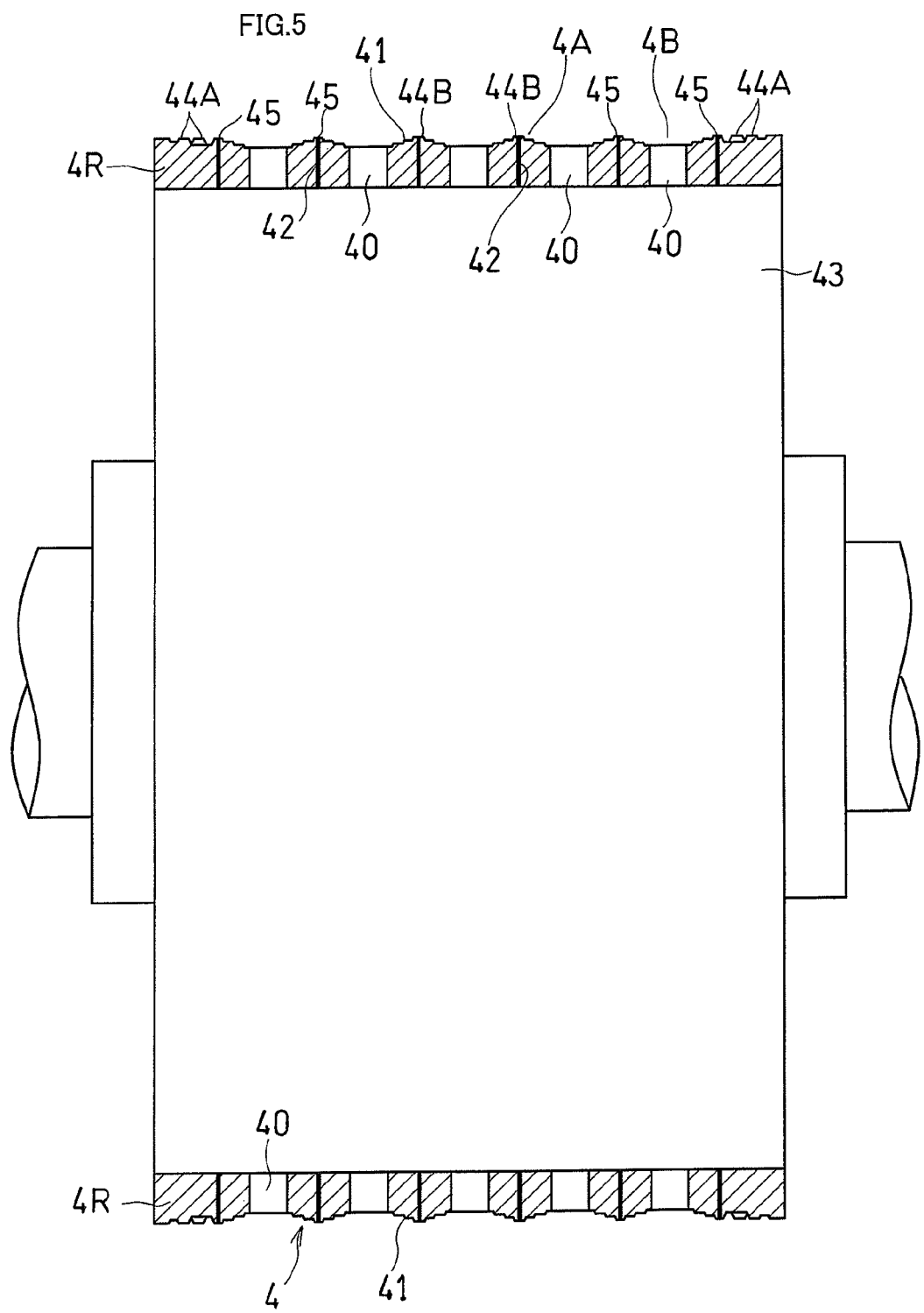

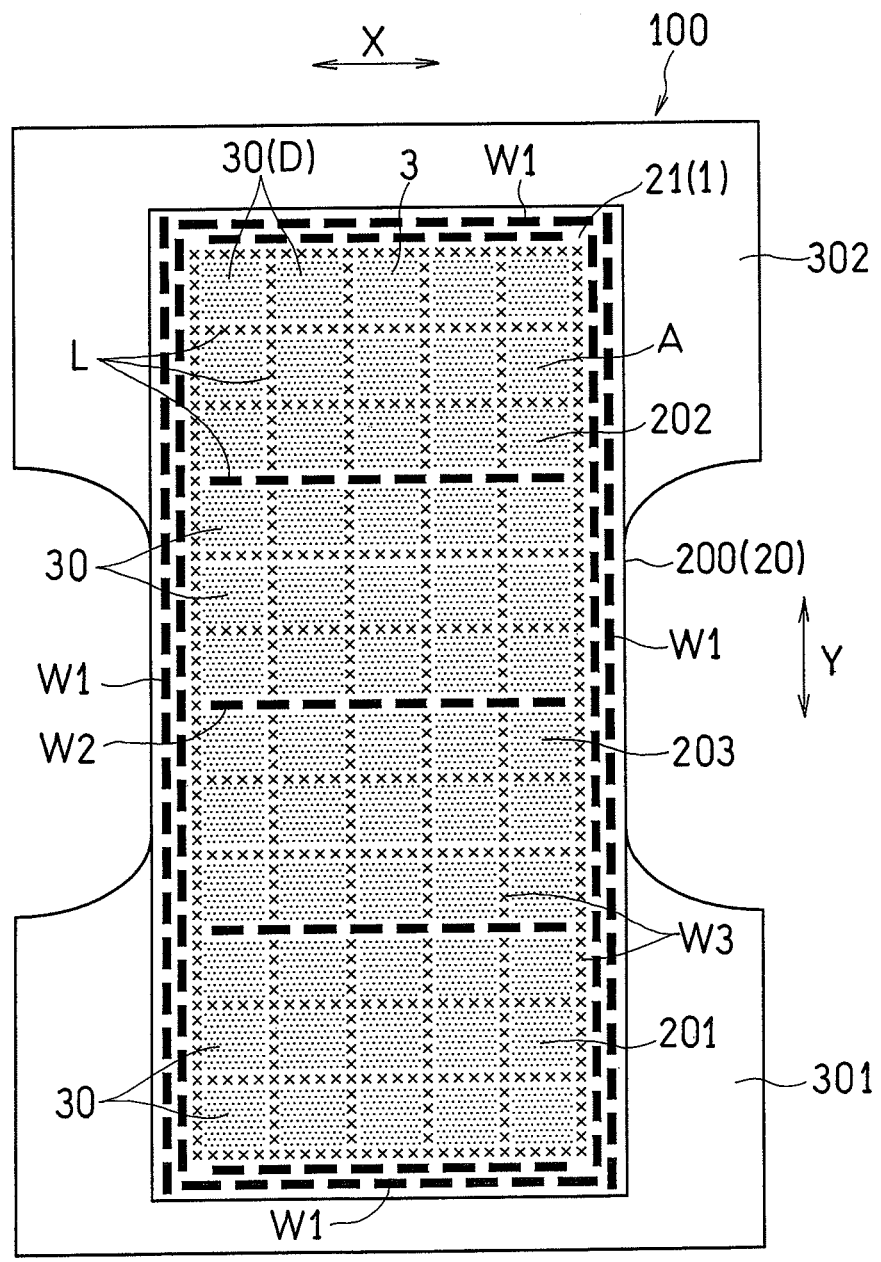

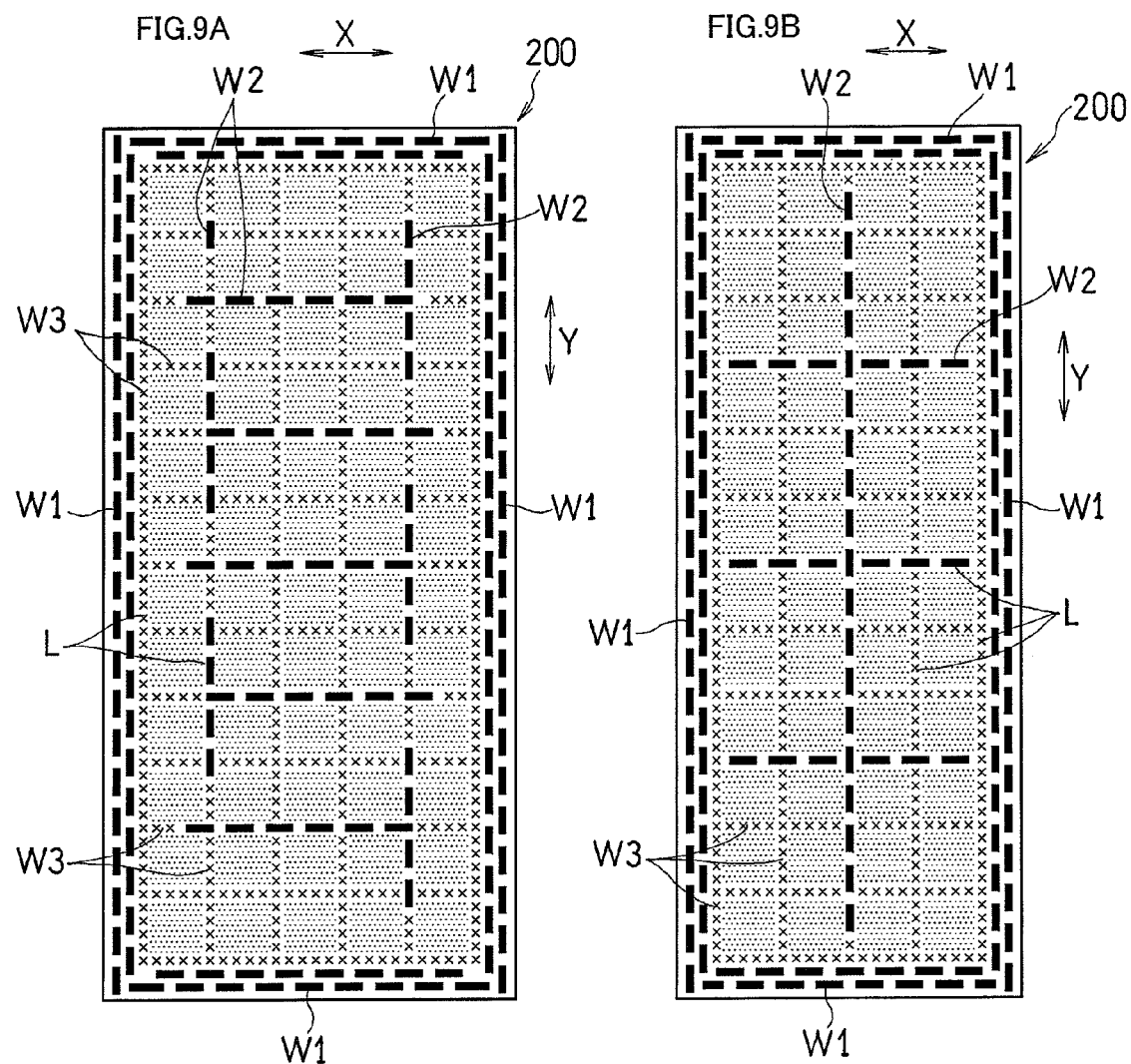

ULTRASONIC BONDING METHOD FOR ABSORBENT ARTICLE, ULTRASONIC BONDING DEVICE FOR ABSORBENT ARTICLE, AND ABSORBENT ARTICLE

TECHNICAL FIELD

The present invention relates to bonding between non-woven fabric sheets of an absorbent article having a large number of granular particles (hereinafter referred to simply as "granular particles") capable of absorbing a body fluid to swell.

BACKGROUND ART

In recent years, absorbent articles have been proposed in the art, in which large amounts of granular particles are confined within a large number of small spaces (the first patent document). In an absorbent article of this type, granular particles are placed in a predetermined pattern between two base sheets, and the base sheets are bonded together along areas where the granular particles are absent.

The bonded portions between the base sheets are bonded with such a low strength that the base sheets are separated from each other by a separating force generated from swelling of a large number of granular particles within an area when the granular particles absorb moisture to swell. Then, the volume of granular particles that can be accommodated between two base sheets can be increased.

CITATION LIST

Patent Literature

[First Patent Document] WO95/11654 A

SUMMARY OF INVENTION

There is no disclosure as to forming both high-strength bonded portions and low-strength bonded portions.

If the base sheets are bonded together only with low-strength bonded portions, a body fluid may leak from the periphery of the absorbent article, or there may arise a need to increase the area of the bonded portion along the periphery.

It is an object of the present invention to provide an absorbent article in which both high-strength bonded portions and low-strength bonded portions are provided, thereby making it possible to increase the amount of granular particles to be accommodated, and making leaks unlikely.

It is also an object of the present invention to provide a method and a device for manufacturing such an absorbent article.

The method of the present invention is an ultrasonic bonding method for use with an absorbent article having a plurality of granular particles, capable of absorbing a body fluid to swell, between two liquid-permeable non-woven fabric sheets facing each other, the method including the steps of:

applying an ultrasonic energy to the two non-woven fabric sheets at some of positions where the granular particles are absent to bond first portions of the two non-woven fabric sheets with each other so as to form at least one high-strength bonded portion such that the two non-woven fabric sheets are not separated from each other at the first portions by a peeling force urging the non-woven fabric sheets to peel off each other; and applying an ultrasonic energy to the two non-woven fabric sheets at other ones of the positions where the granular particles are absent to bond second portions of the two non-woven fabric sheets with each other so as to form at least one low-strength bonded portion such that the two non-woven fabric sheets can be separated from each other at the second portions by the peeling force urging the non-woven fabric sheets to peel off each other.

On the other hand, the present article is an ultrasonic bonding device for use with an absorbent article having a plurality of granular particles, capable of absorbing a body fluid to swell, between two liquid-permeable non-woven fabric sheets facing each other, the ultrasonic bonding device including:

an anvil roll for carrying the two non-woven fabric sheets while the two non-woven fabric sheets are laid on each other;

a plurality of protruding portions formed on the anvil roll so as to protrude outward in a radial direction of the anvil roll;

a placement device for preventing the granular particles from being placed on the non-woven fabric sheets over the protruding portions; and a horn for ultrasonically vibrating so that the two non-woven fabric sheets are bonded together between the horn and the plurality of protruding portions, thereby forming bonded portions, the protruding portions including:

at least one first protruding portion, which is away from the horn by a first distance when the first protruding portion comes closest to the horn, for forming at least one high-strength bonded portion such that the non-woven fabric sheets are not separated from each other at the bonded portion by a peeling force urging the non-woven fabric sheets to peel off each other; and at least one second protruding portion, of which a second distance to the horn when the second protruding portion comes closest to the horn is greater than the first distance, for forming at least one low-strength bonded portion such that the non-woven fabric sheets are separated from each other at the bonded portion by the peeling force urging the non-woven fabric sheets to peel off each other.

The present article obtained by the method of the present invention includes high-strength bonded portions and low-strength bonded portions. When the granular particles absorb a body fluid, the gap between the two non-woven fabric sheets significantly expands, and when the granular particles further absorb a body fluid, a separating force urging the two non-woven fabric sheets to peel off each other is applied to the bonded portions between the two non-woven fabric sheets. This separating force peels the two non-woven fabric sheets off each other at the low-strength bonded portions, thereby increasing the effective volume between the two non-woven fabric sheets, thus allowing the granular particles to further absorb a body fluid.

The present article includes high-strength bonded portions, and the high-strength bonded portions will not be peeled off by the separating force. Therefore, when the high-strength bonded portions are formed along the periphery of the present article, a body fluid will not leak out through between the two non-woven fabric sheets even if the area of the high-strength bonded portions is small. On the other hand, if other high-strength bonded portions different from the high-strength bonded portions formed along the periphery of the present article are provided in an area inside the periphery of the present article, it is possible to prevent the granular particles having absorbed a body fluid from being unevenly distributed (disproportion) between the two non-woven fabric sheets.

The device of the present invention is an ultrasonic bonding device for use with an absorbent article having a plurality of granular particles, capable of absorbing a body fluid to swell, between two liquid-permeable non-woven fabric sheets facing each other, the device including:

an anvil roll for carrying the two non-woven fabric sheets while the two non-woven fabric sheets are laid on each other;

a plurality of protruding portions formed on the anvil roll so as to protrude outward in a radial direction of the anvil roll;

a placement device for preventing the granular particles from being placed on the non-woven fabric sheets over the protruding portions; and a horn for ultrasonically vibrating so that the two non-woven fabric sheets are bonded together between the horn and the plurality of protruding portions, thereby forming bonded portions, the protruding portions including:

at least one first protruding portion, which is away from the horn by a first distance when the first protruding portion comes closest to the horn, for forming at least one high-strength bonded portion such that the non-woven fabric sheets are not separated from each other at the bonded portion by a peeling force urging the non-woven fabric sheets to peel off each other; and at least one second protruding portion, of which a second distance to the horn when the second protruding portion comes closest to the horn is greater than the first distance, for forming at least one low-strength bonded portion such that the non-woven fabric sheets are separated from each other at the bonded portion by the peeling force urging the non-woven fabric sheets to peel off each other.

The ultrasonic energy produced at a first protruding portion, of which the distance to the horn is small, is large, thereby producing a high-strength bonded portion at which the non-woven fabric sheets will not be peeled off each other by the separating force. On the other hand, the ultrasonic energy produced at a second protruding portion, of which the distance to the horn is large, is small, thereby producing a low-strength bonded portion at which the non-woven fabric sheets will be peeled off each other by the separating force.

Absorbent articles, as used in the present invention, refer to feminine sanitary products and incontinence pads, as well as parts such as absorbent bodies and absorbent cores, which are intermediate products of disposable diapers and pants.

BRIEF DESCRIPTION OF DRAWINGS

FIG. 2 is an exploded perspective view showing an absorbent article.

FIG. 5 is a longitudinal cross-sectional view, which is partially a cross-sectional view, showing an example of an anvil roll.

FIG. 8 is a plan view showing another example of a worn article.

FIGS. 9A and 9B are plan views each showing another example of an absorbent article.

Figure 1:
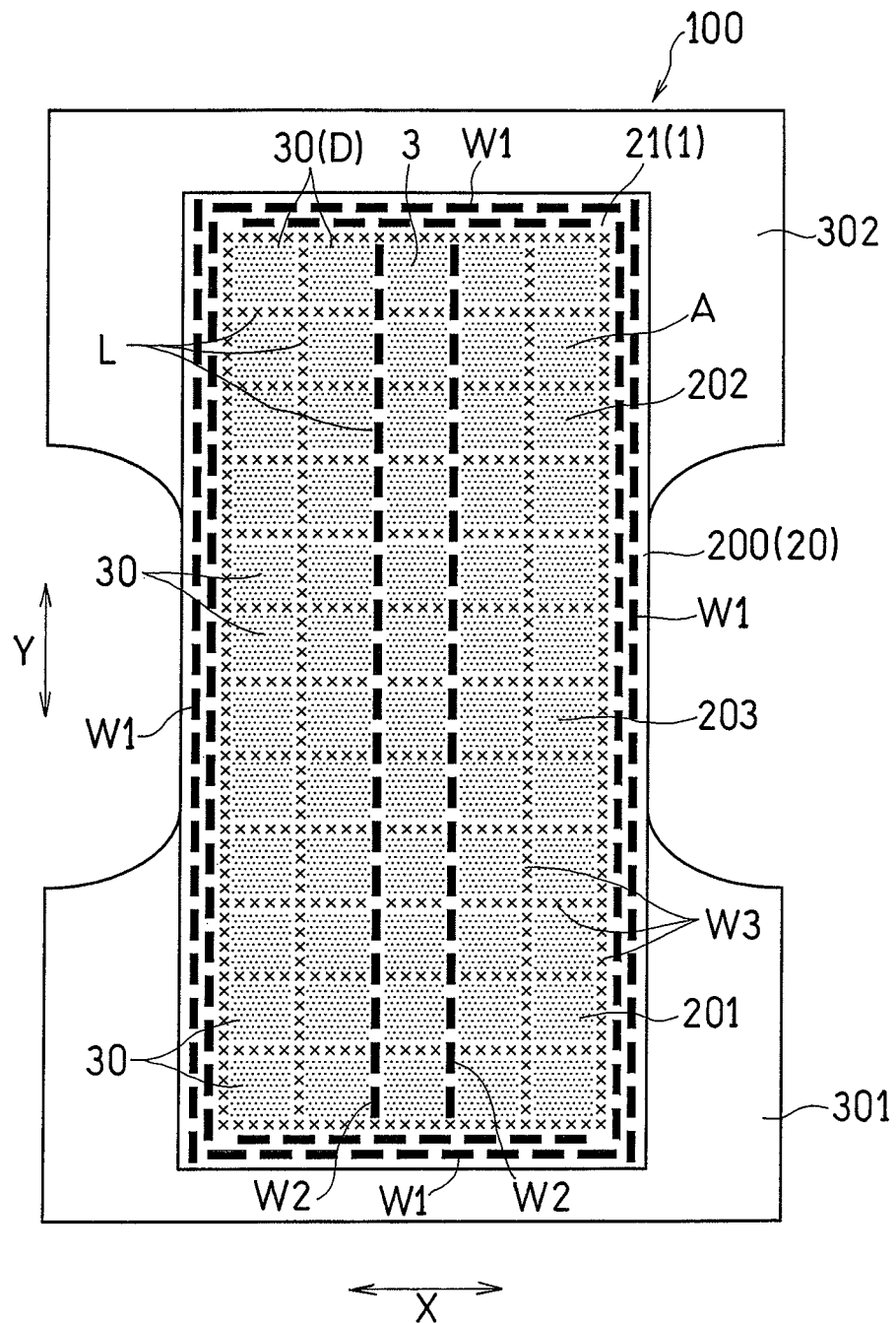
FIG. 1 is a plan view showing a worn article according to Embodiment 1 of the present invention.

Preferably, in the method of the present invention, the step of forming the high-strength bonded portion is performed as the two non-woven fabric sheets pass through between a first protruding portion of an anvil roll for forming the high-strength bonded portion and an ultrasonically-vibrating horn;

the step of forming the low-strength bonded portion is performed as the two non-woven fabric sheets pass through between a second protruding portion of the anvil roll for forming the low-strength bonded portion and the ultrasonically-vibrating horn; and a second distance between the second protruding portion and the horn when the second protruding portion and the horn are facing each other along a normal line of the anvil roll is greater than a first distance between the first protruding portion and the horn when the first protruding portion and the horn are facing each other along the normal line.

In this case, it is possible to produce high-strength bonded portions and low-strength bonded portions with a simple structure that is obtained only by making the heights of the first and second protruding portions provided on the anvil roll different from each other.

Regarding the method of producing the two types of bonded portions in the present invention, it may be possible to produce the two types of bonded portions by, for example, changing the frequency, or providing two horns of different horn widths (lengths in the circumferential direction of the anvil). For example, it may be possible to produce low-strength bonded portions with a first horn of a smaller width, and high-strength bonded portions with a second horn of a larger width.

Preferably, in the method of the present invention, the high-strength bonded portion is formed in a loop-shaped pattern on the article; and the low-strength bonded portion is formed in an inner area surrounded by the high-strength bonded portion.

In this case, with the high-strength bonded portion in the loop-shaped pattern, it is possible to prevent a body fluid from leaking through between the two non-woven fabric sheets, whereas the two non-woven fabric sheets peel off each other at the low-strength bonded portion in the inner area, thereby allowing a large amount of body fluid to be absorbed.

It is more preferred in the method of the present invention that the high-strength bonded portion is formed also in the inner area.

In this case, preferably, the high-strength bonded portion is placed at a position in the inner area between low-strength bonded portions.

In this case, the two non-woven fabric sheets remain bonded at the high-strength bonded portion in the inner area.

Therefore, it is possible to prevent the granular particles having absorbed a body fluid and become heavier from being unevenly distributed.

Preferably, in the device of the present invention, the difference between the first distance and the second distance is generally 3 μm to 60 μm, though it depends also on the weight per unit area of the non-woven fabric sheet. If the distance difference is too small, it will not be possible to obtain an intended bonding strength difference between the high-strength and low-strength bonded portions, and if the distance difference is too large, the bonding strength at the low-strength bonded portions will be too small.

With such reasons, the distance difference is more preferably 10 μm to 30 μm, and most preferably 12 μm to 16 μm, in a case where the weight per unit area of the non-woven fabric sheet is 10 to 20 g/m$^2$.

DESCRIPTION OF EMBODIMENTS

The present invention will be understood more clearly from the description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiment 1

Embodiment 1 of the present invention will now be described with reference to the drawings.

FIGS. 1 to 7 show Embodiment 1.

Worn article 100:

As shown in FIG. 1, the worn article 100 of the present embodiment includes an absorbent body (an example of the absorbent article) 200, a front around-torso member 301, and a back around-torso member 302. The absorbent article 200 includes a front portion 201 covering the front torso of the wearer, a back portion 202 covering the back torso of the wearer, and a crotch portion 203 covering the crotch between the front portion 201 and the back portion 202.

The crotch portion 203 is continuous with the front portion 201 and the back portion 202, and extends in the longitudinal direction Y perpendicular to the girth direction X. The front around-torso member 301 and the back around-torso member 302 may be bonded together when worn, or may be pre-bonded before being worn.

The absorbent article 200 may be provided with three-dimensional gathers (not shown).

The absorbent article 200 may include around-leg portions narrowed in conformity with the legs of the wearer.

Moreover, portions of the absorbent article 200 to be the around-leg portions may be provided with elastic members for fitting the worn article 100 to the wearer. The elastic members may be, for example, a plurality of rubber threads, rubber tapes, a film, a material including a thermoplastic resin, or the like. These material may be provided in the front portion 201 and the back portion 202 as elastic members for fitting the worn article 100 to the wearer.

As shown in FIG. 2, the absorbent article 200 includes a top sheet 21 to be in contact with the skin surface of the wearer, and a cover sheet 22 and an absorbent core 23 to be not in contact with the skin surface. The top sheet 21 and the cover sheet 22 of FIG. 3B (welded portion) are welded together along lattice-shaped welded lines L, L extending in the length and width directions as shown in FIG. 3A, thereby forming a sandwich structure in which the core 23 is sandwiched between adjacent welded lines L, L.

Figure 3A:
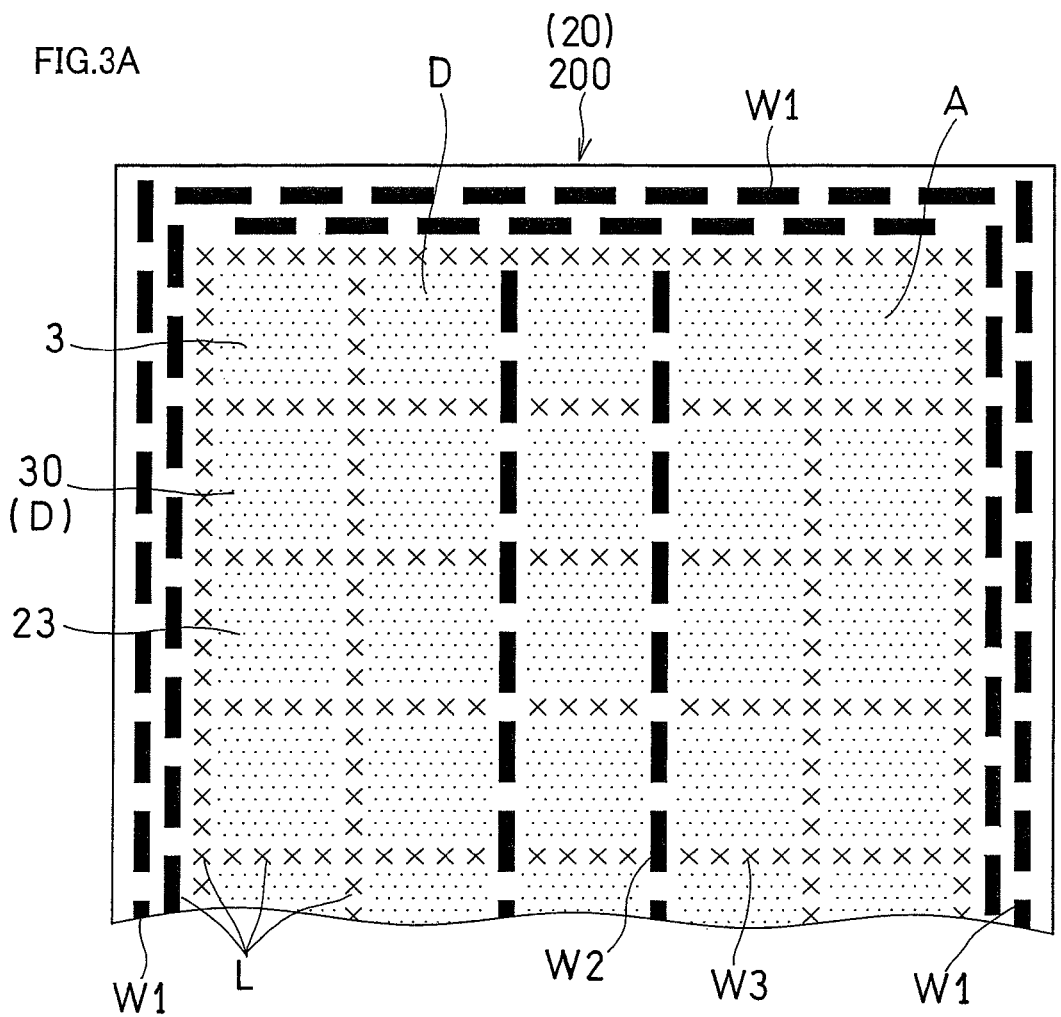
FIG. 3A is a partial enlarged plan view showing the absorbent article.

That is, as shown in FIG. 3A, the core 23 is surrounded by the top sheet 21 and the cover sheet 22 welded together along the welded lines L, L.

Note that welded positions are denoted by 'xx' or small black rectangles in different figures.

Figure 3B:
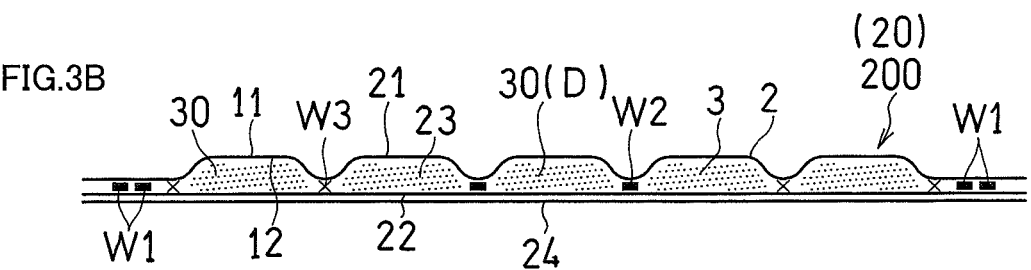
FIG. 3B is a cross-sectional view thereof.

The top sheet 21 and the cover sheet 22 of FIG. 3B are formed by a non-woven fabric sheet that is liquid-permeable and air-permeable. A non-liquid-permeable back sheet 24 is attached to the back surface of the cover sheet 22, and the absorbent article 200 is covered by the back sheet 24.

The core 23 includes a large number of absorbent granular particles 3. The granular particles 3 are made of a well-known absorbent high-molecular polymer whose average granular diameter is typically about 10 μm to about 1,000 μm before absorbing moisture and which swell after absorbing moisture to a volume several times to several hundreds of times larger.

Note that the granular particles 3 are denoted by a large number of minute dots in different figures.

The core 23 includes aggregate groups 30 placed in a large number of placement areas D, the aggregate groups 30 each having an aggregate of a large number of granular particles 3. The aggregate groups 30, 30 are separately arranged in the placement areas D, D partitioned by lattice-shaped welded lines L, L extending in the length and width directions. That is, the placement areas D, D, in which the aggregate groups 30, 30 are placed, are partitioned from one another by the welded lines L, L.

In other words, each aggregate group 30 is composed of an aggregate of a large number of granular particles 3, and the aggregate groups 30 are arranged in the length and width directions with welded lines L, L therebetween, as shown in FIG. 3A. As shown in FIG. 3A, a larger number (three or more) of aggregate groups are arranged in the length and width directions.

A welded line L does not need to be completely continuous, and may be an intermittent array of welded positions such that the granular particles 3 in one aggregate group 30 cannot easily move into other aggregate groups 30.

That is, the welded lines L, L may be formed in such a manner that it is possible to suppress the movement of granular particles 3 from one of the aggregate groups 30, arranged in a predetermined pattern, into another.

The arrangement of the aggregate groups 30 may be any predetermined pattern, and does not need to be a regular array extending in the length and width directions. The number (volume) of granular particles 3 contained in each aggregate group 30 does not need to be generally equal to that in other groups, and the number (volume) of granular particles 3 may be determined based on the amount of body fluid to be discharged in each aggregate group 30.

As shown in the enlarged view of FIG. 3A, the aggregate groups 30 may be rectangular or circular, and the length of each side or the diameter thereof may be some millimeters to some tens of millimeters. The pitch at which the aggregate groups 30, 30 are placed may be about 10 mm to about ten-odd mm.

Next, an important part of the present invention will be described.

In the present embodiment, the welded lines L include first high-strength bonded portions W1, second high-strength bonded portions W2, and low-strength bonded portions W3, as shown in FIG. 3A.

As shown in FIG. 1, the first high-strength bonded portions W1 are formed in a loop-shaped pattern along the periphery of the absorbent article 200, and the first high-strength bonded portions W1 are welded positions (solid black small rectangles) provided in a multi-line staggered array in which they are intermittently formed close to one another, for example.

Note that in different figures showing the first high-strength bonded portions W1, the interval between the rectangular welded positions are shown to be slightly separated in the girth direction X and in the longitudinal direction Y, in order to facilitate the understanding of the manufacturing method. In practice, however, the welded positions are arranged in a staggered array with substantially no gap therebetween in the directions Y and X, and are substantially continuous with one another.

As shown in FIG. 3A, the low-strength bonded portions W3 are placed in a lattice-shaped pattern, for example, in an inner area A surrounded by the first high-strength bonded portions W1 in a loop-shaped pattern, thereby partitioning the inner area A into a plurality of placement areas D as described above. The low-strength bonded portions W3 are denoted by 'xx' in the figures.

The second high-strength bonded portions W2 are formed in a linear pattern, for example, in the inner area A, and may be placed between low-strength bonded portions W3.

That is, as shown in FIG. 1, for example, they may be formed so as to extend in two lines in the longitudinal direction Y in the center of the inner area A surrounded by the first high-strength bonded portion W1.

The second high-strength bonded portions W2 are denoted as solid black rectangles in the figures.

Figure 3C:
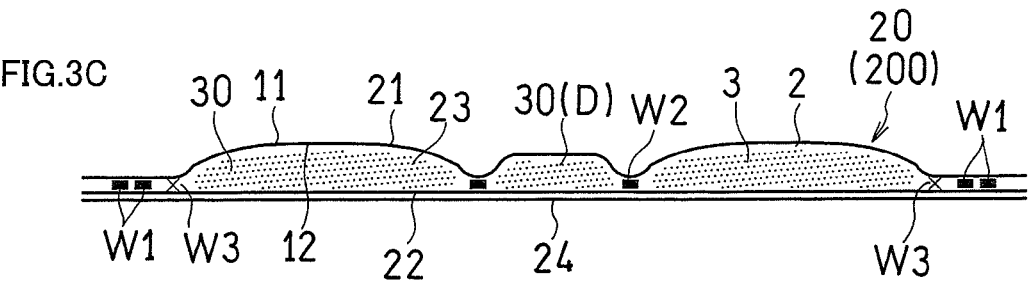
FIG. 3C is a cross-sectional view thereof showing the absorbent article in which two non-woven fabric sheets are separated from each other at low-strength bonded portions.

As shown in FIG. 3C, at the first high-strength bonded portions W1 and the second high-strength bonded portions W2, the top sheet 21 and the cover sheet 22, which are the two non-woven fabric sheets, are welded together with a large welding force such that they will not be separated from each other even when the granular particles 3 swell to apply a separating force to the bonded positions between the sheets 21 and 22.

That is, at the first high-strength bonded portions W1 and the second high-strength bonded portions W2, the top sheet 21 and the cover sheet 22 are welded together with such a large welding force that when there is a peeling force urging the sheets 21 and 22 to peel off each other, the sheets 21 and 22 will not be separated from each other but they will break or a hole will be made in one of the non-woven fabric sheets.

In other words, the first high-strength bonded portions W1 and the second high-strength bonded portions W2 have a strength greater than that of the material of the top sheet 21 and the cover sheet 22, so that if an external force is applied to the sheets 21 and 22, the top sheet 21 or the cover sheet 22 will break due to stress concentration in the vicinity of the first high-strength bonded portions W1 or the second high-strength bonded portions W2.

The first high-strength bonded portions W1 are formed in a loop-shaped pattern along the periphery of the absorbent article 200 and are formed continuously in a staggered array. Therefore, the granular particles 3, a body fluid, or the granular particles 3 having absorbed a body fluid will not leak out through between the top sheet 21 and the cover sheet 22.

At the low-strength bonded portions W3, the two sheets of the top sheet 21 and the cover sheet 22 are welded together with such a small welding force that when the granular particles 3 swell to apply a separating force to bonded positions between the top sheet 21 and the cover sheet 22, the sheets 21 and 22 will be separated from each other at the bonded positions.

That is, the welding force between the non-woven fabric sheets 21 and 22 at the low-strength bonded portions W3 is smaller than the welding force at the first and second high-strength bonded portions W1 and W2.

Therefore, when a body fluid from the wearer is absorbed by the granular particles 3 through the top sheet 21 of FIG. 3B, the granular particles 3 swell substantially so that a pressure acts upon the space between the top sheet 21 and the cover sheet 22 as shown in FIG. 3B, thereby separating the top sheet 21 and the cover sheet 22 from each other at the low-strength bonded portions W3 as shown in FIG. 3C, thus enabling further liquid absorption by the granular particles 3.

Thus, even where the absorbent body 200 has a small thickness before being used, it is possible to absorb a large amount of body fluid.

Note that the low-strength bonded portions W3 provided adjacent to the inner side of the first high-strength bonded portions W1 as shown in FIG. 3C only receive a separating force acting from one side. Therefore, even if the granular particles 3 swell, the separation may occur there later than at the other low-strength bonded portions W3 or the separation may not occur there. These low-strength bonded portions W3 may be omitted.

On the other hand, the second high-strength bonded portions W2 remain bonded even after the granular particles 3 swell. This restricts the granular particles 3, having swollen and become heavier, from moving freely in the inner area A.

That is, the swollen granular particles 3 are restricted within regions defined by the first high-strength bonded portions W1 and the second high-strength bonded portions W2.

Therefore, it will be possible to prevent the granular particles 3 from being significantly unevenly distributed in the inner area A.

As shown in FIG. 1, the placement area D may be surrounded only by the low-strength bonded portions W3, or may be surrounded by the low-strength bonded portions W3 and the second high-strength bonded portions W2.

Where those low-strength bonded portions W3 that are adjacent to the inner side of the first high-strength bonded portions W1, provided along the periphery of the article 200, are absent, the placement area D may be surrounded by the first high-strength bonded portions W1 and the low-strength bonded portions W3. Alternatively, the placement area D may be surrounded by the first high-strength bonded portions W1, the second high-strength bonded portions W2, and the low-strength bonded portions W3.

Note that the non-woven fabric sheet may be a thermoplastic resin non-woven fabric sheet such as polypropylene, polyethylene, polyester, or the like, and it may also be a non-woven fabric sheet obtained by blending together non-thermoplastic fibers such as cotton or rayon with thermoplastic resin fibers.

Next, a device for manufacturing the absorbent article 200 will be illustrated.

Figure 4A:
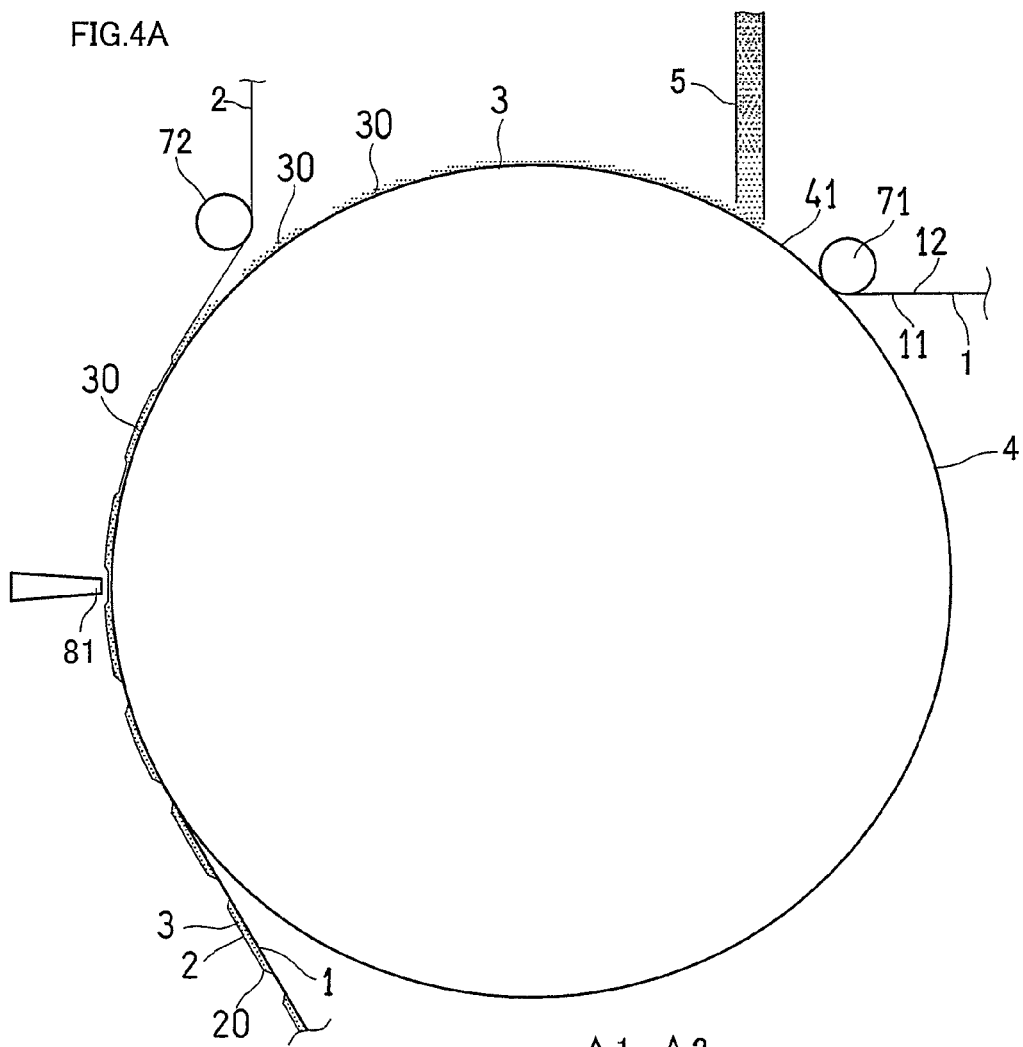
FIGS. 4A and 4B are side views each showing a device for manufacturing the absorbent article.

As shown in FIG. 4A, the present device includes a dispenser device 5, first and second introduction rolls 71 and 72, and an ultrasonic horn 81, arranged around an anvil roll 4.

The first and second introduction rolls 71 and 72 are rolls for introducing a carrier web 1 and a cover web 2, respectively, onto the outer circumference of the anvil roll 4.

The top sheet 21 and the cover sheet 22 of the absorbent article 200 (FIG. 2) are produced from the carrier web 1 and the cover web 2, respectively.

The anvil roll 4 carries the carrier web 1 along a predetermined carrying path while holding by suction a first surface 11 of the air-permeable carrier web 1 on a carrying surface 41. The first surface 11 forms the skin surface to be in contact with the skin of the wearer.

The dispenser device 5 dispenses myriads of granular particles 3 onto a second surface 12 opposite to the first surface 11 of the carrier web 1 being carried, downstream of the first introduction roll 71.

The myriads of granular particles 3 are dispensed intermittently or continuously so that a predetermined amount is dispensed per unit area of the carrier web 1.

As shown in FIGS. 6A to 7B, a large number of suction holes 40 (an example of the placement device) are provided (open) in suction areas 4B of the carrying surface 41. Each suction hole 40 communicates with a suction source (negative pressure source) (not shown), and draws a first air $\alpha 1$ of FIG. 6B into the suction hole 40 through the carrier web 1, thereby holding by suction the granular particles 3 on the second surface 12 of the carrier web 1 of FIG. 4A.

A plurality of suction holes 40 and a plurality of suction areas 1B are provided so as to define a plurality of placement areas D of FIG. 1, which are placed in a predetermined pattern. The plurality of placement areas D are areas in which aggregates of granular particles are placed while being partitioned from one another.

As shown in FIGS. 5 to 7B, discharge holes 42 (an example of the placement device) are provided (open) in non-suction areas 4A, where the suction is absent, including first and second protruding portions 44B and 45 between the suction holes 40 and the suction holes 40, on the anvil roll 4. Each discharge hole 42 is open in the first and second protruding portions 44B and 45 of the carrying surface 41 for discharging a second air $\alpha 2$.

The discharge holes 42 may be absent in first protruding portions 44A. The provision of the discharge holes 42 is not necessary because substantially no granular particles 3 are dispensed along the periphery of the carrier web 1 if the width over which the granular particles 3 are dispensed from the dispenser device 5 is substantially the same as the width over which the granular particles 3 are placed in the absorbent article 200.

Note that the first protruding portions 44A may be provided with the discharge holes 42, similar to the first protruding portion 44B and the second protruding portion 45.

Note that the discharge holes 42 formed in the protruding portions 44B and the protruding portions 45 are indicated by thick black lines in FIG. 5 in order to facilitate the understanding of the structure.

Figures 6A, 6B:
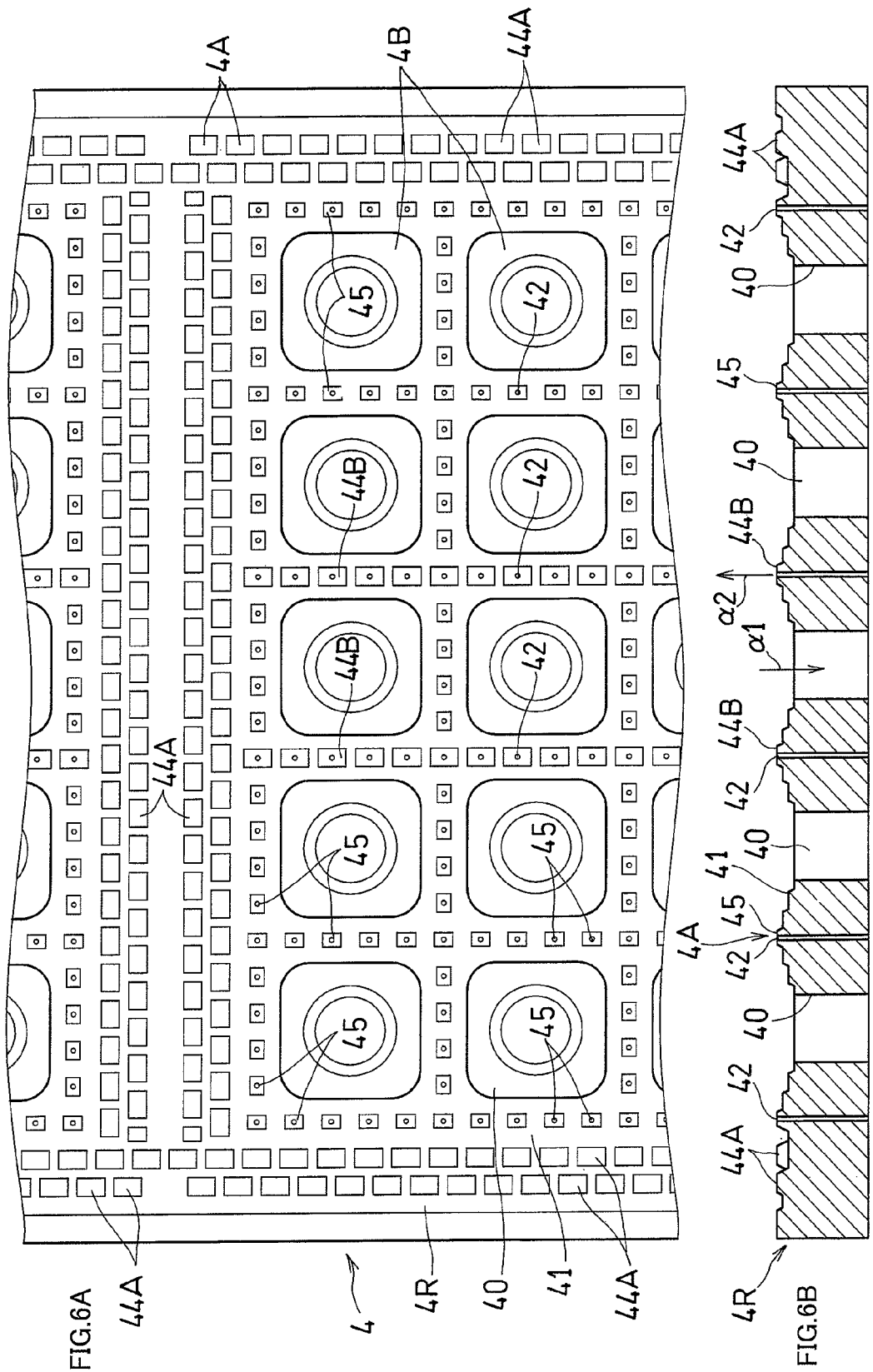
FIG. 6A is a development view showing a part of the outer circumferential surface of the anvil roll unfolded onto a plane.
FIG. 6B is a longitudinal cross-sectional view showing a ring forming the outer circumferential portion of the anvil roll.

Each discharge hole 42 communicates with a positive pressure source (not shown) and discharges the second air $\alpha 2$ from the discharge hole 42 toward the second surface 12 of the carrier web 1 of FIG. 4A, so that the granular particles 3 are blown away off non-suction areas 1A (corresponding to the non-suction areas 4A) on the carrier web 1, where the suction is absent, by the second air $\alpha 2$ of FIG. 6B having passed through the carrier web 1 via the second surface 12.

Thus, the suction holes 40 and the discharge holes 42 prevent the granular particles 3 from being placed on the carrier web 1 over the protruding portions 44A, 44B and 45.

As shown in FIG. 4A, the granular particles 3 dispensed from the dispenser device 5 onto the carrier web 1 are partitioned into the aggregate groups 30 by the placement device (the suction holes 40 and the discharge holes 42) as the carrier web 1 is carried downstream.

After the granular particles 3 are placed on the carrier web 1, the second introduction roll 72 of FIG. 4A introduces the cover web 2 onto the carrying path at a position of the carrier web 1 downstream in the carrying path in order to produce a sandwich structure 20 (FIG. 7B) in which the second surface 12 of the carrier web 1 and the granular particles 3 are covered by the cover web 2.

The anvil roll 4 carries the sandwich structure 20 as described above.

That is, as shown in FIG. 4A, the cover web 2 is introduced after the granular particles 3 are partitioned into the aggregate groups 30 on the carrier web 1. The cover web 2 covers portions of the second surface 12 of the carrier web 1 where the granular particles 3 are absent, and the granular particles 3 placed on the carrier web 1. Thus, the sandwich structure 20 is produced.

Note that due to the first air $\alpha 1$ drawn into the suction holes 40 of the anvil roll 4 of FIG. 6B, the cover web 2 introduced over the second surface 12 and the granular particles 3 are bowed into the anvil roll 4.

The anvil roll 4 may include a roll body 43 and a ring-shaped anvil 4R removably attached over the outer circumference of the roll body 43, as shown in FIG. 5. Then, it is possible to easily change the placement pattern, or the like.

As shown in FIGS. 6A to 7A, a large number of first protruding portions 44A and 44B and second protruding portions 45 are provided around the suction holes 40 of the anvil 4R. These protruding portions 44A, 44B and 45 are protruding outward in the radial direction of the anvil roll 4, and are facing the ultrasonic horn 81 (FIG. 4A) with the sandwich structure 20 therebetween as the anvil roll 4 rotates.

Figure 7A:
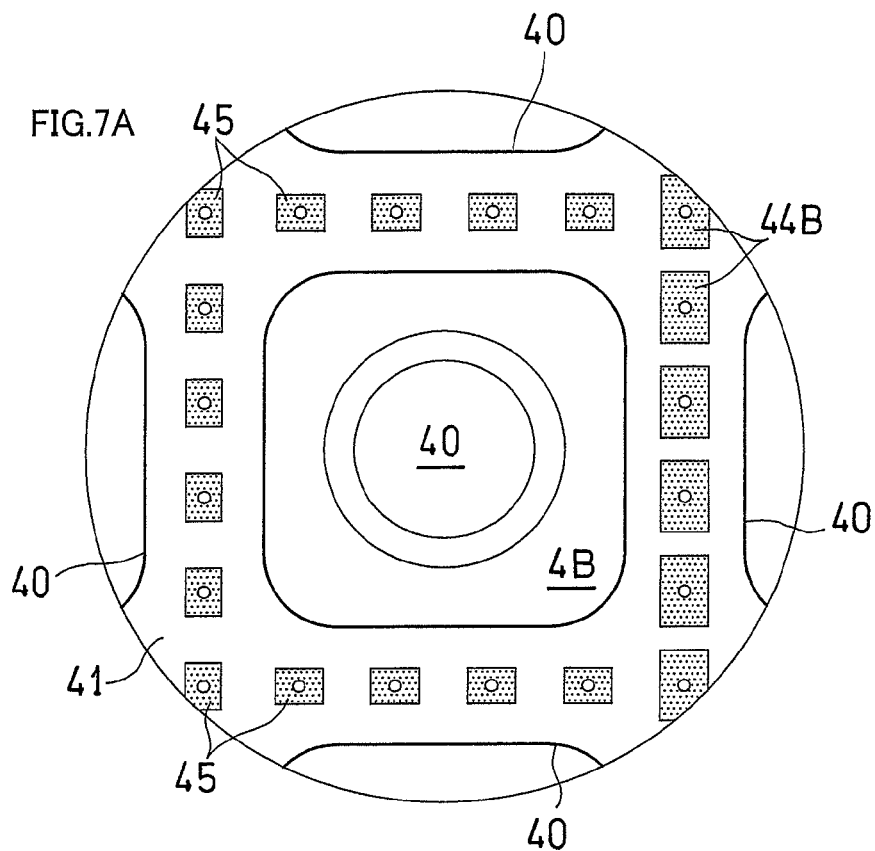
FIG. 7A is a development view showing, on an enlarged scale, a part of the anvil roll.
Figure 7B:
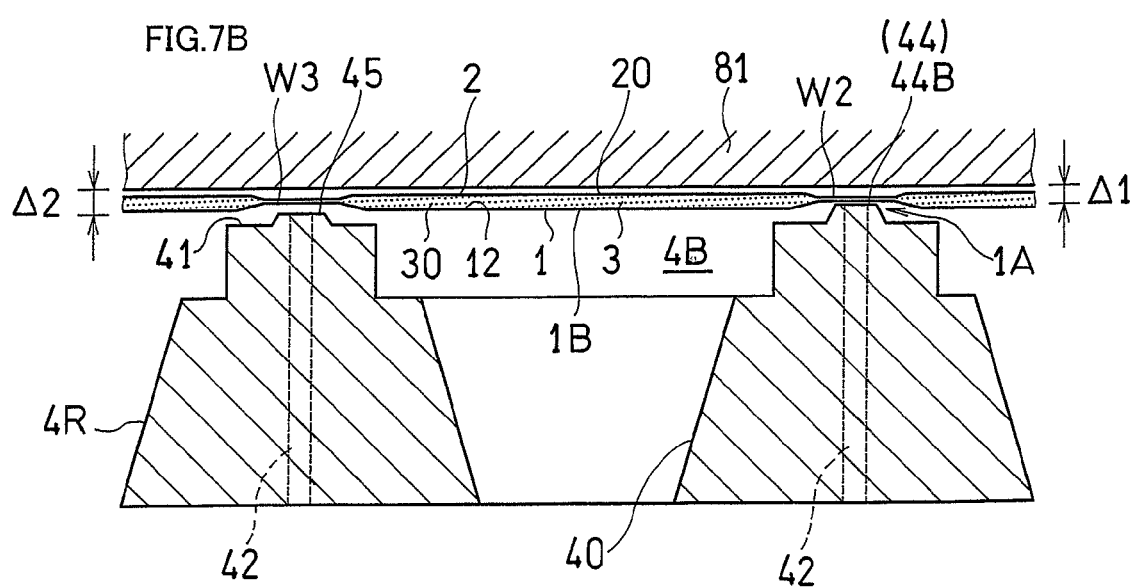
FIG. 7B is a longitudinal cross-sectional view showing, on an enlarged scale, an absorbent article passing through between the anvil roll and a horn.

As shown in FIG. 7B in an exaggerated manner, the first distance $\Delta 1$ from the first protruding portion 44 (the protruding portion 44A or 44B) to the horn 81 is small when the first protruding portion 44 and the horn 81 are facing each other along the normal line NL (FIG. 4B) of the anvil roll 4. The reason why the first distance $\Delta 1$ is small is to form high-strength bonded portions (the high-strength bonded portions W1 or W2) at positions where the non-woven fabric sheets (the carrier web 1 and the cover web 2) are bonded together, such that the carrier web 1 and the cover web 2 will not be separated from each other by a peeling force urging the webs 1 and 2 to peel off each other.

On the other hand, the second distance $\Delta 2$ from the second protruding portion 45 to the horn 81 when the second protruding portion 45 and the horn 81 are facing each other along the normal line NL (FIG. 4B) of the anvil roll 4 is larger than the first distance $\Delta 1$. The reason why the second distance $\Delta 2$ is large is to form low-strength bonded portions W3 at positions where the non-woven fabric sheets (the carrier web 1 and the cover web 2) are bonded together, such that the webs 1 and 2 will be separated from each other by a peeling force urging the webs 1 and 2 to peel off each other.

That is, the first protruding portions 44B (or the first protruding portions 44A) are protruding toward the horn 81, i.e., outward in the radial direction, more than the second protruding portions 45.

Note that the first protruding portion 44B is shown in FIG. 7B to be protruding more than the second protruding portion 45 in an exaggerated manner in order to facilitate the understanding of the structure.

Where the second protruding portions 45 are present in the width direction, perpendicular to the circumferential direction, of the outer circumference surface of the anvil 4R of FIG. 6A, the first protruding portions 44A and 44B may be placed at at least one location or at a plurality of locations. With such an arrangement, the horn 81 strongly contacts the first protruding portions 44A and 44B with the webs 1 and 2 (FIG. 7B) therebetween and softly contacts the second protruding portions 45. Therefore, it will be possible to easily realize intended bonding strengths for the high-strength bonded portions W1 and W2 and for the low-strength bonded portions W3 of FIG. 1.

Therefore, in the article 100 of FIG. 1, it is preferred that at least one or a plurality of high-strength bonded portions W1 and W2 are present at the same position in the longitudinal direction Y at which the low-strength bonded portions W3 are present.

Figure 4B:
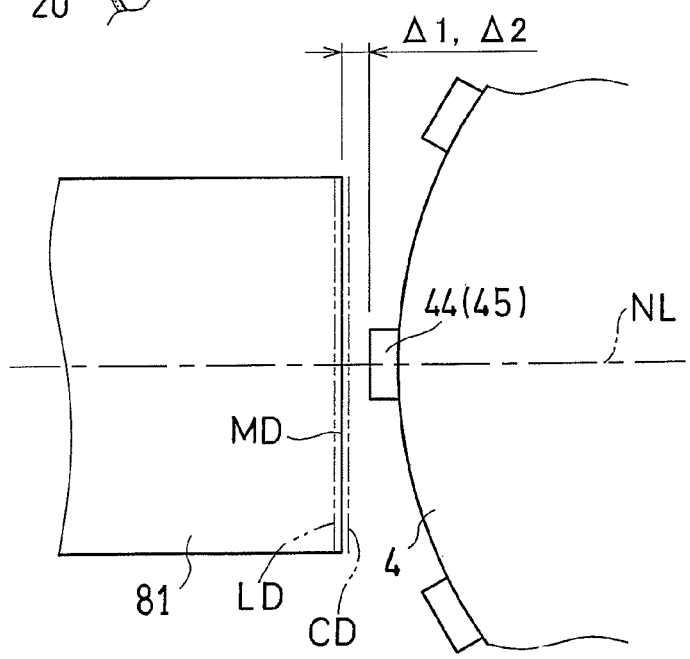

As shown in FIG. 4B, the first distance $\Delta 1$ (or the second distance $\Delta 2$) is the distance between the center of the first protruding portion 44 (44A, 44B) (or the second protruding portion 45) and the center of the horn 81 when they are facing each other along the normal line NL of the anvil roll 4. The distance $\Delta 1$ (or $\Delta 2$) is the distance between the horn 81 and the protruding portion 44A, 44B (or 45) when the vibrating horn 81 is at the middle position MD between the position LD thereof where the horn 81 is farthest away from the anvil roll 4 and the position CD thereof where the horn 81 is closest to the anvil roll 4.

Note that various elements are shown in FIG. 4B in an exaggerated manner in order to facilitate the understanding of the relationship between the protruding portions 44 and 45 formed on the anvil roll 4 and the horn 81.

The settings of the first distance $\Delta 1$ and the second distance $\Delta 2$ should be determined based on various conditions, such as the weight per unit area of non-woven fabric sheets to be welded, the pressing load by which the horn is pressed against the anvil, and the capacity of the welder. For example, where the weight per unit area of the non-woven fabric sheet 21 is 10 g/m$^2$ and the weight per unit area of the non-woven fabric sheet 22 is 10 g/m$^2$, the first distance $\Delta 1$ may be set to be about 50 μm and the second distance $\Delta 2$ may be set to be about 65 μm.

Note that the difference $\Delta$ between the distances $\Delta 1$ and $\Delta 2$ may be generally set to be about 12 μm to about 16 μm.

As is partially shown in FIG. 6A, the first protruding portions 44A are placed on the anvil roll 4 so that the first high-strength bonded portions W1 (FIG. 1) are formed in a loop-shaped pattern along the periphery of the absorbent article 200.

On the other hand, the first protruding portions 44B of FIG. 6A are placed on the anvil roll 4 so as to form the second high-strength bonded portions W2 in the inner area A of FIG. 1.

The second protruding portions 45 of FIG. 6A are placed on the anvil roll 4 so that the low-strength bonded portions W3 of FIG. 1 are formed in the inner area A surrounded by the first high-strength bonded portions W1.

That is, the first high-strength bonded portions W1, the second high-strength bonded portions W2 and the low-strength bonded portions W3 are formed along positions where the first protruding portions 44A, the first protruding portions 44B and the second protruding portions 45 are placed, respectively.

As shown in FIG. 4A, the ultrasonic horn 81 gives the vibration energy to the webs 1 and 2 in cooperation with the ring-shaped anvil 4R (FIG. 5), which forms the carrying surface 41 of the anvil roll 4, downstream of the second introduction roll 72 in the carrying path of the carrier web 1. Thus, the carrier web 1 and the cover web 2 are welded together at the first protruding portions 44B (44A) and the second protruding portions 45 of FIG. 7B.

With welding (sealing) using ultrasonic vibrations, mechanical vibrations are ultrasonically transmitted to the horn 81 of FIG. 4A, so that thermoplastic non-woven fabric sheets pass through between the horn 81 and the anvil 4R while being pressurized, thereby welding the non-woven fabric sheets (the carrier web 1 and the cover web 2) with each other by frictional heat. Therefore, a seal failure is likely to occur if granular particles 3, which are foreign matters, remain between the webs 1 and 2 in the non-suction areas 4A of FIG. 6A.

Next, an outline of a method for manufacturing the sandwich structure 20 will be described.

As shown in FIG. 4A, the carrier web 1 is introduced onto the anvil roll 4 by the first introduction roll 71, and the carrier web 1 is carried along a predetermined carrying path, i.e., the carrying surface 41 of the carrying drum 4, while the first surface 11 of the carrier web 1 is held by suction on the carrying surface 41 of the anvil roll 4.

Between the first introduction roll 71 and the second introduction roll 72, a large number of granular particles 3 are dispensed from the dispenser device 5 onto the second surface 12, opposite to the first surface 11, of the carrier web 1 which is being carried. The dispensed granular particles 3 form a layer on the second surface 12.

As the first air $\alpha 1$ is drawn toward the suction holes 40 formed in the anvil 4R shown in FIG. 6B, the dispensed granular particles 3 are held by suction on the carrier web 1.

Note that an airflow deflector may be provided opposing the second surface 12 of the carrier web 1, the airflow deflector giving at least a part of the first air $\alpha 1$ a flow component flowing in a direction along the second surface 12 of the carrier web 1. (PCT/JP2012/52371)

The layer of granular particles 3 of FIG. 4A may be dispensed intermittently for each absorbent body 200 (FIG. 1).

The layer of granular particles 3 may have a greater thickness in the central part of the layer than in opposite end portions of the layer in the axial direction of the anvil roll 4. Alternatively, the layer of granular particles 3 may have a smaller thickness along the periphery of one absorbent body 200 (FIG. 1) and have a greater thickness in the center or the vicinity thereof.

In FIGS. 6A to 7B, the first air $\alpha 1$ is drawn through the carrier web 1 by a plurality of suction holes 40 formed in the carrying surface 41, as described above, thereby holding by suction some of the granular particles 3 on the second surface 12 of the carrier web 1.

On the other hand, while the first air $\alpha 1$ is drawn, the second air $\alpha 2$ is discharged toward the second surface 12 of the carrier web 1 from the discharge holes 42 open in the non-suction areas 4A including the protruding portions 44B and 45 of the carrying surface 41.

By simultaneously drawing the first air $\alpha 1$ and discharging the second air $\alpha 2$, the granular particles 3 on the non-suction areas 1A are blown away by the second air $\alpha 2$ having passed through the carrier web 1 via the second surface 12, and the blown granular particles 3 are drawn by the first air $\alpha 1$ toward the suction areas 1B over the suction holes 40.

As shown in FIG. 7B, the granular particles 3 in the non-suction areas 1A on the carrier web 1 move into the suction areas 1B so that the granular particles 3 are placed in a predetermined pattern on the carrier web 1.

That is, some granular particles 3 in the non-suction areas 1A move toward other granular particles 3 being sucked and held in the suction areas 1B. As a result, as shown in FIG. 1, the aggregate groups 30, each including a plurality of granular particles 3, are placed on the carrier web 1 separately in the placement areas D partitioned in a predetermined pattern.

As shown in FIG. 4A, after the granular particles 3 dispensed from the dispenser device 5 are placed in a predetermined pattern (separately in the placement areas D) on the carrier web 1, the second surface 12 of the carrier web 1 where the granular particles 3 are absent, and the granular particles 3 placed on the carrier web 1 are covered by the cover web 2 introduced by the second introduction roll 72, thereby producing the sandwich structure 20.

Then, as the sandwich structure 20 continues to be rotated by the carrying surface 41 to reach the ultrasonic horn 81 of FIG. 4A, the carrier web 1 and the cover web 2 are ultrasonically welded together at positions corresponding to the non-suction areas 1A of FIG. 2.

Thus, the predetermined pattern of the granular particles 3 is maintained. After welding together the webs 1 and 2, the suction of the suction holes 40 and the discharge from the discharge holes 42 of FIG. 6B may be stopped. During the welding process, the back sheet 24 of FIG. 3B is also welded onto the cover web 2, but the back sheet 24 may be bonded with an adhesive onto the cover web 2 after the carrier web 1 and the cover web 2 are welded together.

Then, the sandwich structure 20 is cut into individual worn articles, i.e., into individual absorbent bodies 200 of FIG. 1.

Next, an important part of the method of the present invention will be described.

During the ultrasonic welding process of FIG. 7B, the first distance Δ1 between the horn 81 and the first protruding portion 44A, 44B (FIG. 6B) is small, and the welding energy is high accordingly, so that the first and second high-strength bonded portions W1 and W2 (FIG. 3B) are formed, where the non-woven fabric sheets (the top sheet 21 and the cover sheet 22) will not be separated by the separating force.

On the other hand, during the ultrasonic welding process, the second distance Δ2 between the horn 81 and the second protruding portion 45 is larger than the first distance Δ1, and the welding energy is low accordingly, so that the low-strength bonded portions W3 are formed, where the non-woven fabric sheets 21 and 22 will be separated from each other by the separating force.

As a body fluid is absorbed by the absorbent article 200 having such high-strength bonded portions W1 and W2 and such low-strength bonded portions W3 of FIG. 3B, the granular particles 3 swell with the body fluid, thereby expanding the gap between the top sheet 21 (non-woven fabric sheet) and the cover sheet 22 (non-woven fabric sheet).

The separating force from the expansion of the granular particles 3 peels the top sheet 21 and the cover sheet 22 from each other as shown in FIGS. 3B and 3C in the low-strength bonded portions W3, where the welding strength is weak. This allows the granular particles 3 to swell further, allowing for the absorption of a large amount of body fluid between the top sheet 21 and the cover sheet 22.

On the other hand, along the second high-strength bonded portions W2, the top sheet 21 and the cover sheet 22 remain welded even if the separating force is applied. Therefore, where the absorbent body 200 is partitioned by the first high-strength bonded portions W1 and the second high-strength bonded portions W2 as shown in FIG. 1, the granular particles 3, having absorbed a body fluid and become heavier, are prevented from being significantly unevenly distributed (disproportion) left and right.

The second high-strength bonded portions W2 are not completely continuous with one another so that a body fluid or the granular particles 3 are allowed to move from any placement area D surrounded by the second high-strength bonded portions W2 into another placement area D adjacent to that placement area D. This prevents the internal pressure in any particular placement area D from becoming high.

Moreover, as shown in FIG. 3C, for the first high-strength bonded portions W1 placed along the periphery of the absorbent article 200, the top sheet 21 (non-woven fabric sheet) and the cover sheet 22 (non-woven fabric sheet) remain welded even if the separating force is applied. Moreover, the first high-strength bonded portions W1 are formed in a double-line linear pattern, thereby completely sealing between the top sheet 21 and the cover sheet 22. Therefore, a body fluid is prevented from leaking out through between the top sheet 21 and the cover sheet 22.

Note that black rectangles indicating the first high-strength bonded portions W1 are shown with exaggerated large intervals therebetween in order to facilitate the understanding of the manufacturing method as described above.

As shown in FIG. 8, the second high-strength bonded portions W2 may be provided so as to extend in the girth direction X, not in the longitudinal direction Y. As shown in FIGS. 9A and 9B, second high-strength bonded portions W2 extending in the longitudinal direction Y and second high-strength bonded portions W2 extending in the girth direction X may both be provided.

As shown in FIGS. 1, 8 and 9B, the second high-strength bonded portions W2 may be provided so as to completely partition a plurality of placement areas D.

On the other hand, the second high-strength bonded portions W2 may be provided so as to extend partially in the girth direction X and/or the longitudinal direction Y without partitioning the placement areas D. For example, as shown in FIG. 9A, high-strength bonded portions W2 extending in the girth direction X and high-strength bonded portions W2 extending in the longitudinal direction Y may be placed in a T-shaped pattern.

Moreover, the first high-strength bonded portions W1 do not need to be provided parallel to the girth direction X and the longitudinal direction Y.

Moreover, the placement of the high-strength bonded portions W2 and the low-strength bonded portions W3 may be any combination of those of FIG. 1 and FIGS. 9A to 9B.

As is clearly shown in FIG. 7A, non-continuous protruding portions 44B may be used to form non-continuous second high-strength bonded portions W2 of FIG. 3A. Continuous protruding portions, such as the protruding portion 44A of FIG. 6A, may be used to form continuous second high-strength bonded portions W2 in a staggered array.

Note that if the second high-strength bonded portions W2 are non-continuous, there will be less stiffness and a better wearability, and it will also be advantageous for pressure adjustment between placement areas D.

While preferred embodiments have been described above with reference to the drawings, obvious variations and modifications will readily occur to those skilled in the art upon reading the present specification.

For example, with the present article, the method for bonding the top sheet 21 and the cover sheet 22 with each other may be thermal welding such as heat seal, for example, instead of ultrasonic welding.

As used in the present invention, "a plurality of granular particles" is a concept including cases where a powdery material is mixed with a plurality of granular particles, as well as cases where they are made only of an aggregate or aggregates of a granular material.

Thus, such changes and modifications are deemed to fall within the scope of the present invention, which is defined by the appended claims.

INDUSTRIAL APPLICABILITY

The present invention is applicable to disposable worn articles, such as feminine sanitary products and incontinence pads, as well as disposable diapers and disposable pants.

REFERENCE SIGNS LIST

1: Carrier web, 1A: Non-suction area, 1B: Suction area, 11: First surface, 12: Second surface 2: Cover web, 20: Sandwich structure, 21: Top sheet (non-woven fabric sheet), 22: Cover sheet (non-woven fabric sheet), 23: Core, 24: Back sheet 3: Granular particles, 30: Aggregate group, D: Placement area 4: Anvil roll, 4A: Non-suction area, 4B: Suction area, 40: Suction hole, 41: Carrying surface, 42: Discharge holes (an example of the placement device), 4R: Anvil, 43: Roll body, 44A, 44B: First protruding portion, 45: Second protruding portion 5: Dispenser device 71: First introduction roll, 72: Second introduction roll 81: Ultrasonic horn 100: Worn article, 200: Absorbent body (absorbent article), 201: Front portion, 202: Back portion, 203: Crotch portion, 301: Front around-torso member, 302: Back around-torso member A: Inner area α1: First air, α2: Second air X: Girth direction, Y: Longitudinal direction, NL: Normal line W1: First high-strength bonded portion, W2: Second high-strength bonded portion, W3: Low-strength bonded portion Δ1: First distance, Δ2: Second distance

The invention claimed is:
1. An ultrasonic bonding device for use with an absorbent article having a plurality of granular particles, capable of absorbing a body fluid to swell, between two liquid-permeable non-woven fabric sheets facing each other, the device comprising:
an anvil roll for carrying the two non-woven fabric sheets while the two non-woven fabric sheets are laid on each other;
a plurality of protruding portions formed on the anvil roll so as to protrude outward in a radial direction of the anvil roll;
a placement device for preventing the granular particles from being placed on the non-woven fabric sheets over the protruding portions; and
a horn for ultrasonically vibrating so that the two non-woven fabric sheets are bonded together between the horn and the plurality of protruding portions, thereby forming bonded portions, the protruding portions comprising:
at least one first protruding portion, which is away from the horn by a first distance when the first protruding portion comes closest to the horn, for forming at least one high-strength bonded portion such that the non-woven fabric sheets are unseparated from each other at the bonded portion by a peeling force urging the non-woven fabric sheets to peel off each other; and
at least one second protruding portion, of which a second distance to the horn when the second protruding portion comes closest to the horn is greater than the first distance, for forming at least one low-strength bonded portion such that the non-woven fabric sheets are separatable from each other at the bonded portion by the peeling force urging the non-woven fabric sheets to peel off each other,
wherein a difference between the first distance and the second distance is 3 μm to 60 μm.
2. The ultrasonic bonding device according to claim 1, wherein:
the first protruding portion is placed on the anvil roll so that the high-strength bonded portion is formed in a loop-shaped pattern on the article; and
the second protruding portion is placed on the anvil roll so that the low-strength bonded portion is formed in an inner area surrounded by the high-strength bonded portion.
3. The ultrasonic bonding device according to claim 2, wherein the first protruding portion includes a first protruding portion placed on the anvil roll for forming another high-strength bonded portion different from the high-strength bonded portion formed in the loop-shaped pattern.
4. The ultrasonic bonding device according to claim 3, wherein:
the first protruding portion and/or the second protruding portion are provided so that the low-strength bonded portion and/or the high-strength bonded portions define a plurality of placement areas partitioned from one another in a predetermined pattern; and
the placement device places a plurality of granular particles separately in the placement areas.

* * * * *